United States Patent [19]
Fabian

[11] Patent Number: 5,307,397
[45] Date of Patent: * Apr. 26, 1994

[54] FILM CASSETTE HAVING MARKER FOR IDENTIFYING THE EXPOSURE SIDE OF A MEDICAL RADIOGRAPH

[76] Inventor: Carl E. Fabian, 577 NE. 96th St., Miami Shores, Fla. 33138

[*] Notice: The portion of the term of this patent subsequent to Dec. 31, 2008 has been disclaimed.

[21] Appl. No.: 915,242

[22] Filed: Jul. 20, 1992

Related U.S. Application Data

[63] Continuation-in-part of Ser. No. 791,778, Nov. 4, 1991, Pat. No. 5,189,689, which is a continuation of Ser. No. 572,392, Aug. 27, 1990, Pat. No. 5,077,778.

[51] Int. Cl.$^5$ .............................................. H05G 1/28
[52] U.S. Cl. .................................. 378/162; 378/165; 378/166
[58] Field of Search ............... 378/165, 166, 162, 182, 378/181, 185, 187

[56] References Cited

U.S. PATENT DOCUMENTS

| | | | |
|---|---|---|---|
| 4,698,836 | 10/1987 | Minasian | 378/162 |
| 5,070,248 | 12/1991 | Pesce | 378/182 |
| 5,086,445 | 2/1992 | Fisher et al. | 378/165 |
| 5,189,689 | 2/1993 | Fabian | 378/162 |

Primary Examiner—David P. Porta
Assistant Examiner—Kim-Kwok Chu
Attorney, Agent, or Firm—Ernest D. Buff

[57] ABSTRACT

The present invention provides an X ray film cassette with a permanent marking means for identifying the side of the radiographic film that faced the X ray tube during exposure. Such identification does not require any action by the X ray technologist, eliminating the element of human error. The marking means is comprised of chirally asymmetric X ray opaque and/or light-opaque letters or markings permanently mounted in the film cassette to intersect overlapping portions of an X ray path projected during exposure.

17 Claims, 6 Drawing Sheets

FILM CASSETTE HAVING MARKER FOR IDENTIFYING THE EXPOSURE SIDE OF A MEDICAL RADIOGRAPH

CROSS-REFERENCE TO RELATED APPLICATIONS

This application is a continuation-in-part of copending U.S. application Ser. No. 791,778 filed Nov. 4, 1991, now U.S. Pat. No. 5,189,689, which, in tern, is a continuation of U.S. application Ser. No. 572,392, filed Aug. 27, 1990, now U.S. Pat. No. 5,077,778.

BACKGROUND OF THE INVENTION

1. Field of the Invention

The present invention relates to the field of medical radiography; and more particularly to means for positively identifying the exposure side or front side of an X ray film.

2. Description of the Prior Art

A medical radiograph is the X ray image of some part of the body produced by an X ray beam originating from an X ray tube. The X ray beam passes first through the body and then through an X ray film cassette which is a light-proof, flat box of rigid construction. It is typically comprised of a base with a central recess to receive the film, and a cover joined to the base by hinges and containing latches permitting it to be opened and securely closed when a film is loaded. In order to diminish the X ray dose required to obtain a proper exposure of the film the inside surfaces of the cassette are lined with "intensifying screens" which sandwich the film between them. The X ray beam passing through the intensifying screens causes them to fluoresce and give off visible light which in turn exposes the film from both sides. Since the X ray film is much more sensitive to the visible light than to the X ray beam, most of the film exposure actually results from the induced light. The presence of the screens therefore allows the optimal film exposure to be achieved at significantly lower radiation doses than would otherwise be needed. Once the film is exposed, it is brought to the dark room, removed from the cassette and developed, causing the latent image to become visible. The radiograph is then ready for viewing and interpretation.

Since the film must be identified with pertinent information such as patient's name, date, etc., the cassette is also provided with what is herein called a "blocker". This blocker is generally comprised of two opposing strips of lead mounted on the inside surfaces of the cassette which shield the area of film between them from becoming exposed by either the X ray beam or its induced light. When the technologist is ready to develop the film, a card bearing the appropriate patient data is placed into a device which light-flashes the card, thereby projecting the data onto the unexposed area shielded by the blocker. The position of the blocking rectangle within the cassette is not constant and may vary with the manufacturer, individual X ray department, and even from one cassette type to another within the same department.

Apparatus and methods, including modifications of the film cassette for marking exposed X ray film or radiographs with patient data are disclosed, for example by U.S. Pat. Nos. 3,628,864, 3,703,272, 4,465,364, 4,510,392, 4,806,959, 4,383,329, 4,520,497, and 4,768,114.

When rendering a diagnosis from a radiograph it is necessary for the film reader to know which side of the body is being viewed. Since the body is generally symmetrical, right-sided structures are similar in appearance to left-sided structures except that they are mirror-images or reversals of one another. For example, an X ray image of a left foot if viewed from the back /f the exposed film will look like a right foot. Since radiographs are typically transparent and can be viewed from either side, it is therefore possible for X ray images of one side of the body to become confused with the other. For this reason when a medical radiograph is performed of some part of the body it is customary for the technologist to affix and X ray opaque "R" or "L" marker on the cassette cover adjacent to the part being X-rayed to indicate which side of the body is represented on the film. Not infrequently however, the technologist places the wrong marker on the cassette or for one reason or another the marker is not visible on the film, being either obscured or omitted, so that the technologist is required to mark the film after it is developed, using an adhesive label, wax pencil, ink, or even scratch marks. The incidence of incorrect or absent right/left marking due to human error is quite substantial, reportedly as high as 30%. If a film is improperly marked and the physician interpreting the film recognizes the error he will often try to locate the technologist who performed the study to obtain clarification. When the question cannot be resolved in this manner, the patient may be recalled for a repeat examination which involves time, inconvenience, expense and additional radiation exposure. Furthermore, if the error should go undetected, inappropriate medical treatment may be the result.

Since the primary cause of this right/left confusion stems from the fact that the film is transparent and may be viewed from the front (exposure side) or the back, identifying the front side of the film for the viewer will prevent the inadvertent viewing of the film from the wrong side and thereby permit ready determination of which side of the body is represented thereon.

There is no means described in the prior art for permanently modifying the film cassette to expressly indicate the exposure side of the film, positively and regardless of the direction of exposure.

SUMMARY OF THE INVENTION

The present invention provides an X ray film cassette with a permanent marking means for identifying the side of the radiographic film that faced the X ray tube during exposure. Such identification does not require any action by the X ray technologist, eliminating the element of human error. In a preferred embodiment, the working means is comprised of chirally asymmetric X ray opaque and/or light-opaque letters or markings permanently mounted in the film cassette.

Generally stated, markers are permanently mounted in the film cassette, providing the cassette with means for marking the X ray film during exposure with an image indicating the side of the film which faced the X ray tube during exposure.

In one aspect, the invention provides a radiographic film cassette for exposing a sheet of film to X rays projected along an X ray path by an X ray tube. The cassette includes a cover having an inner surface defining a recess for receiving the film sheet. A base having an inner surface is adapted to close upon the cover, securing the film sheet. The cassette has a &irst intensifying screen immovably disposed within the recess between the film sheet and the inner surface of the cover. A first marker is permanently fixed to the first intensifying screen and adjacent to the film to intersect a first portion of the X ray path during exposure. The first marker is chirally asymmetric and light opaque. A second marker is permanently fixed to the second intensifying screen adjacent to the film for intersecting a second portion of the X ray path. The second marker is light opaque, has external dimensions greater than the first marker and is so situated within the X-ray path that the first portion is overlapped by the second portion. The film sheet, upon exposure, bears a composite image of both the first and second markers. Optionally, the first and second marker are formed by removing a part of their respective intensifying screens. Alternatively the second marker is chirally asymmetric and light opaque, and the first marker is light opaque and has external dimensions greater than the second marker.

In addition, the invention provides an apparatus for installing a plurality of light-opaque markers on active sides of a plurality of intensifying screens disposed in an X ray film cassette, comprising; first and second markers, each being light-opaque and at lest one being chirally asymmetric; first and second appliqué sheets carrying the first and second markers, respectively, each of the appliqué sheets having an adhesive surface in contact with an anti-stick protective sheet, adapted for removal to unmask adhesive thereon; and spacing means comprising a spacer sheet having first and second planar surfaces provided with adhesive adapted for temporary contact with the first and second appliqué sheets, respectively, to thereby form a marker installation assembly; whereby disposition of the marker installation assembly on an active side of one of the intensifying screens with the adhesive surfaces unmasked is operative, upon closing the cassette, to adhesively secure the appliqué sheets to the intensifying screens in an aligned condition.

In use, the invention provides information concerning identification of the X ray path leading to exposure of the film sheet, which positively identifies the exposure side or front of the film. The information is provided by means which are user friendly and virtually eliminate the element of human error. Positive identification of the side of the film sheet facing the X ray tube during exposure permits more accurate diagnosis and results in fewer repeat examinations, thereby reducing the attendant inconvenience, expense and total radiation exposure to the population at large and improving the quality of medical care. Additionally, the information is copied to reproductions of the film.

BRIEF DESCRIPTION OF THE DRAWINGS

The invention will be more fully understood and further advantages will become apparent when reference is made to the following detailed description of the preferred embodiment of the invention and the accompanying drawings, in which.

DESCRIPTION OF THE PREFERRED EMBODIMENTS

Figure 1:
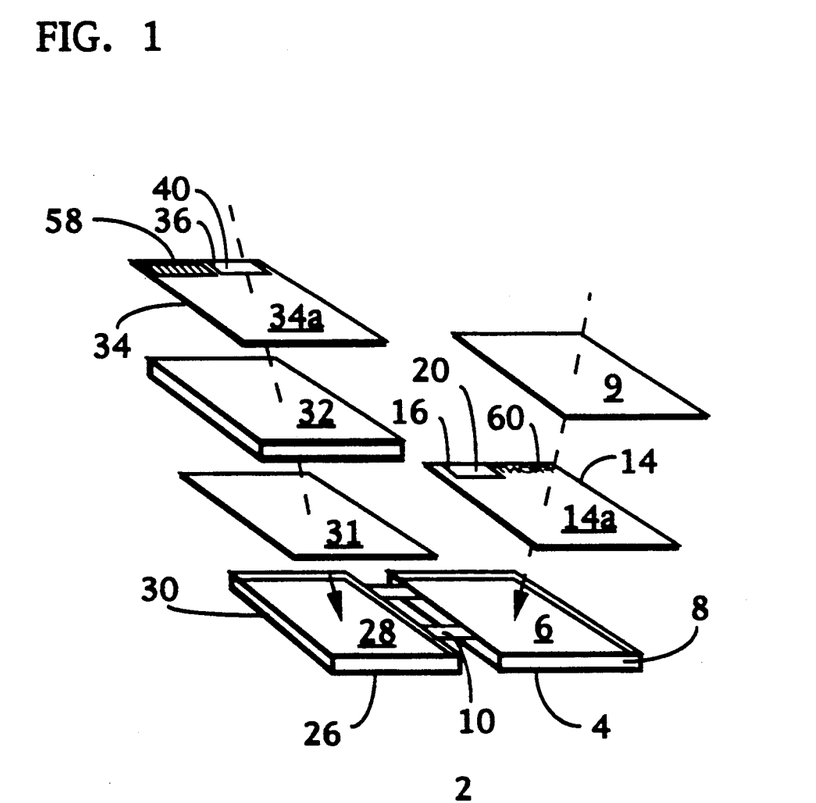
FIG. 1 is an exploded view of an X ray film cassette.
Figure 2:
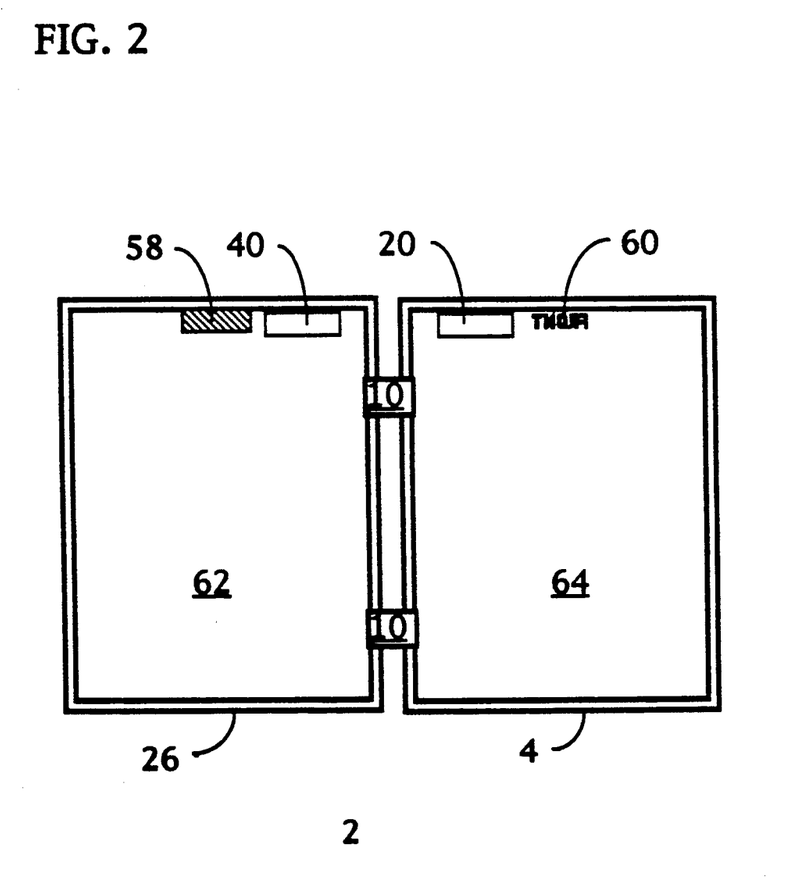
FIG. 2 is a view of the inside of an open cassette equipped with stand-alone light-opaque markers.

Referring to FIGS. 1 and 2 of the drawings, there is shown an X ray film cassette 2 having molded cover 4 of aluminum, plastic, or other suitable material which is transparent to X rays and which is of rigid construction. Cover 4 has a flat inner surface 6 and upstanding flanges 8 encompassing the periphery of surface 6 to provide a recess for receiving a sheet of film 9. One or more hinges 10 are mounted along one of the flanges for attaching a base 26. A first intensifying screen 14 having an active surface 14a comprising a fluorescent material is attached to the inner surface 6. The first intensifying screen 14 is provided with a rectangular cutout 16 along one edge to receive X ray opaque blocking rectangle 20. Typically, blocking rectangle 20 comprises lead sheet of approximately 1 inch by 3 inches. A molded base 26 is formed of aluminum, plastic or other suitable material which is of rigid construction. Base 26 has a flat inner surface 28 and upstanding flanges 30 encompassing the periphery of surface 28 to provide a recess for receiving film sheet 9. Flange 30 is connected along one side to hinges 10. A foam pad 32 attached to the inner surface 28 of base 26 carries a second intensifying screen 34 having an active surface 34a comprising a fluorescent material. The second intensifying screen 34 has a cutout 36 provided to receive a second blocking rectangle 40. Typically, blocking rectangle 40 comprises lead sheet of approximately 1 inch by 3 inches. A sheet of lead 31 may be interposed between pad 32 and inner surface 28. Typically, cutout 36 and blocking rectangle 40 are identical to their respective counterparts 16 and 20 in cover 4 and are arranged so that the blocking rectangles 20 and 40 are stacked one over the other when the cassette 2 is closed.

First marker 60 and second marker 58 are located on the inner surfaces of intensifying screens 14 and 34, and generally along the edge thereof. Markers 60 and 58 are comprised of light-opaque material, such as black ink, paint, printed decal or similar marking, or X ray opaque lead foil. Marker 60 is chirally asymmetric. Chiral asymmetry provides a marker with a mirror image that is different from itself. Preferably, marker 60 comprises a symbol that expressly indicates the front or exposure side of the film, such as "F", "FRONT", VIEWING SIDE, TUBE SIDE, EXPOSURE SIDE, etc., since film 9 is normally viewed from the exposure side. Letters such as B, C, D, etc., and almost any word or sequence of words or letters in which the mirror image is different are chirally asymmetric and can be utilized. On the other hand, isolated letters such as "A", "O", "I", "T" and words such as "XIX", by virtue of their chiral symmetry would not be suitable. Cutting away or removing a portion of the intensifying screen in the desired shape would have the same effect. The dimensions of marker 58 are greater than the dimensions of marker 60. Markers 58 and 60 are oriented such that they line up one over the other when cassette 2 is closed, and marker 60 reads properly if viewed through cover 4.

Alternatively the second marker 58 is chirally asymmetric and light opaque, and the first marker 60 is light opaque and has external dimensions greater than the second marker. As a further alternative, markers 60 and 58 are cut out from their respective intensifying screens 14 and 34.

Figure 3:
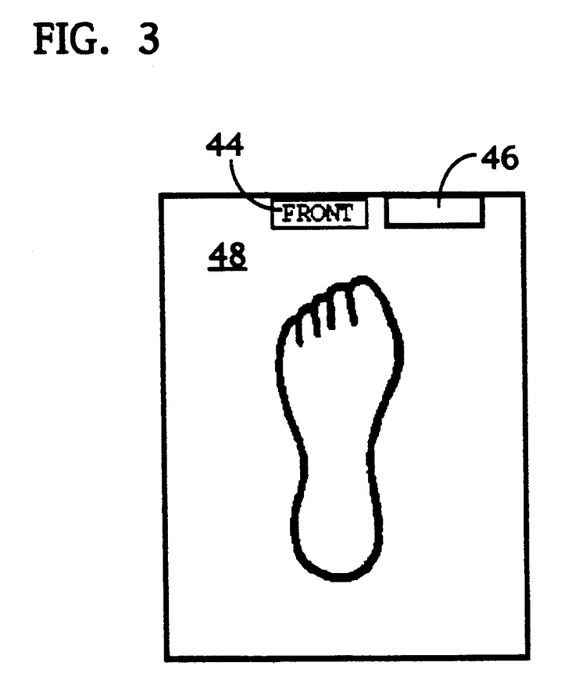
FIG. 3 is an exposure-side view of an X ray film.
Figure 4:
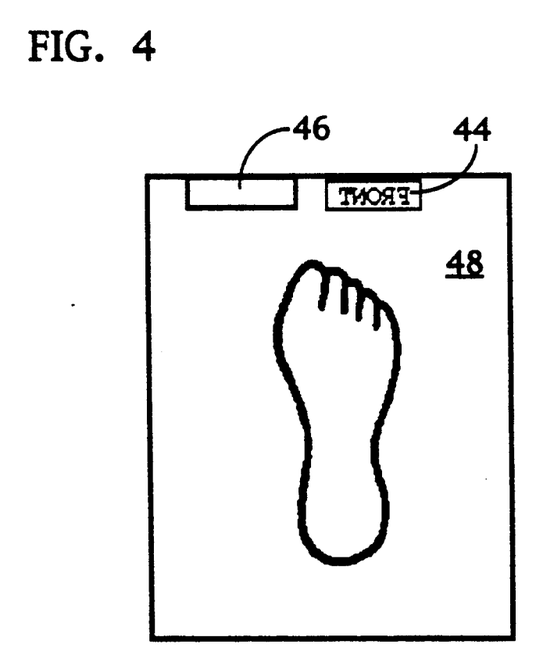
FIG. 4 is a view from the back of an X ray film.

A radiograph of a left foot exposed in the usual way, through the cover of the cassette, is shown in FIGS. 3 and 4. When viewed from the front or exposure side of film 48, as shown in FIG. 3, marker image 44 is readable and the anatomy of the foot is also displayed in the correct orientation. Conversely, when film 48 is viewed from the back side, as shown in FIG. 4, the orientation of the anatomy is reversed, making it appear like a right foot, but the marker image 44 is also reversed, warning that the view is from the back side of film 48. Blocking rectangle image 46 is also shown in the figures.

Figure 5:
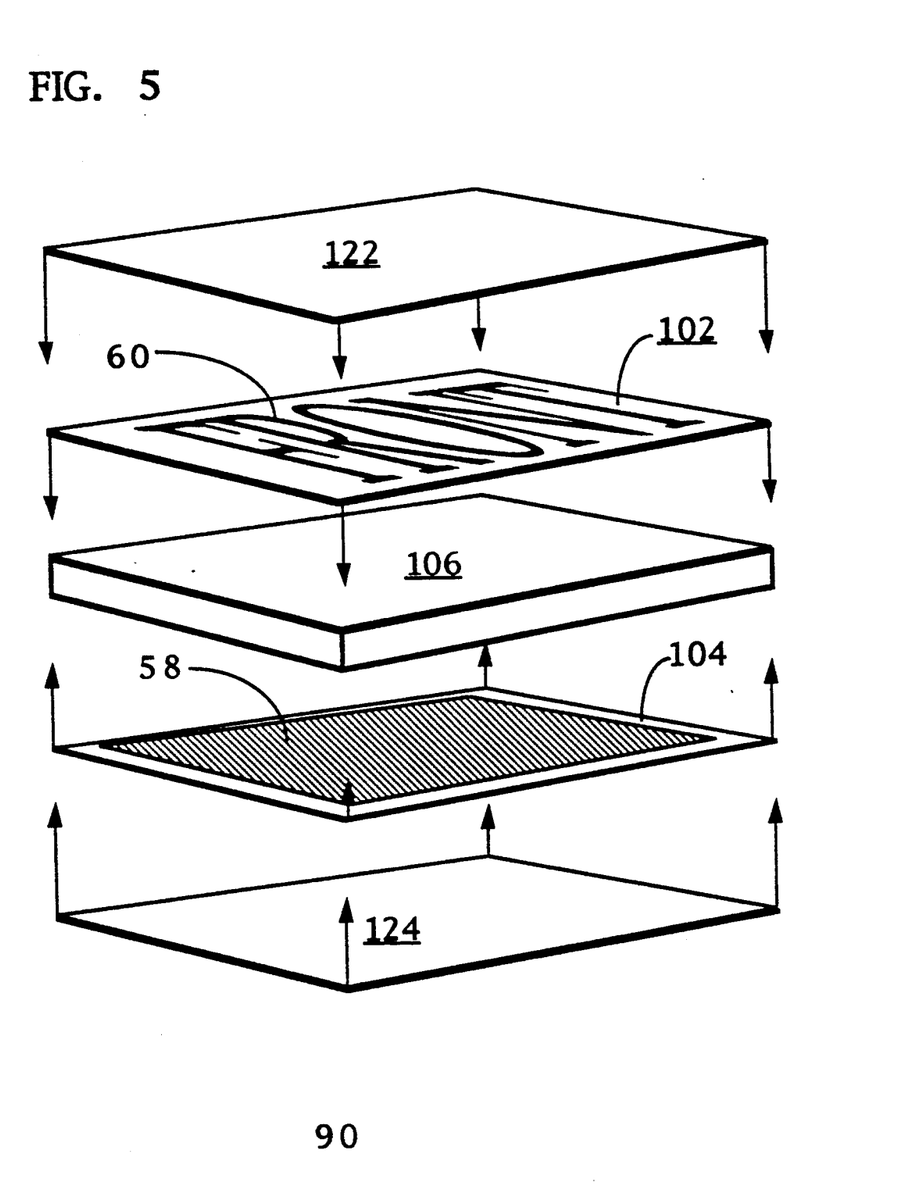
FIG. 5 is an exploded view of apparatus for installing light-opaque markers on intensifying screens.
Figure 6:
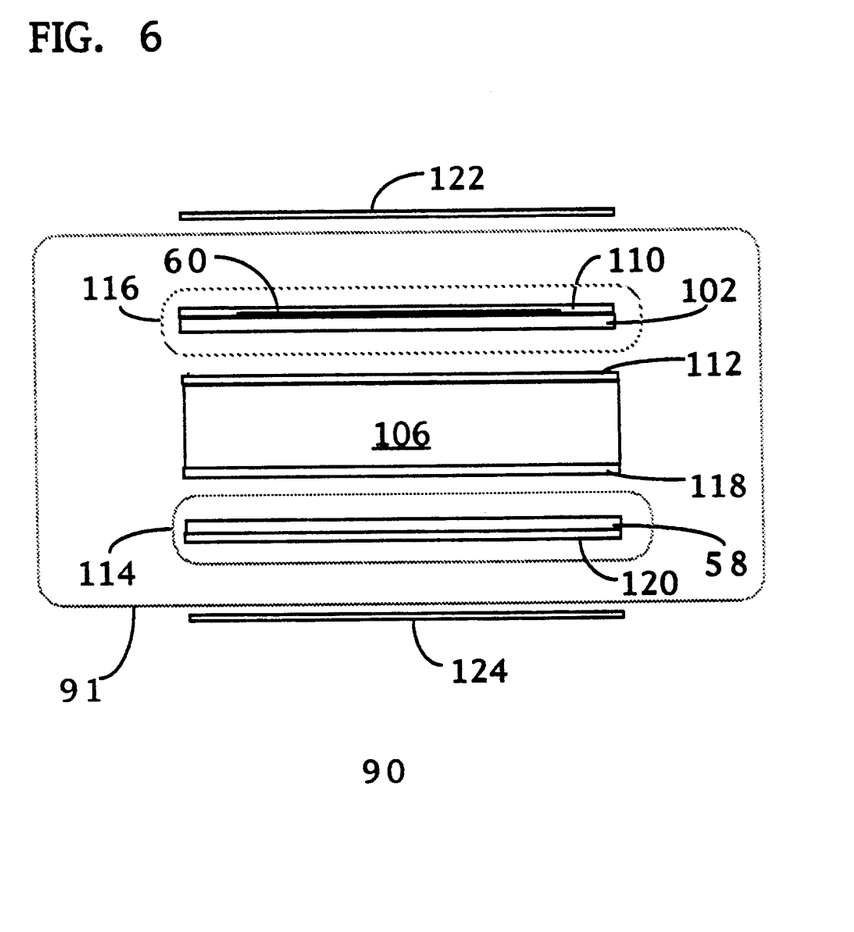
FIG. 6 is a side view of the apparatus shown in FIG. 5.

Shown in FIGS. 5 and 6 is an apparatus 90 to facilitate installation of light-opaque markers 58 and 60 in cassette 2, the apparatus being about ⅛ inch in thickness. Apparatus 90 comprises a marker installation assembly 91 and anti-stick protective sheets 122 and 124. Appliqué 116 comprises light-transparent or translucent sheet 102, light-opaque marker 60, and permanent, adhesive coating 110, such as a pressure sensitive adhesive. Similarly, appliqué 114 comprises light-transparent or translucent sheet 104, light-opaque marker 58, and permanent, adhesive coating 120. Preferably, the adhesive coatings 110 and 120 exhibit clarity and resistance to ultraviolet and X ray aging, such as but not limited to, polyvinyl ethyl ether, polyisobutylene, or acrylate copolymer based coatings. The sheets 102 and 104 are composed of a member selected from the group consisting of cellophane, polyvinyl chloride, polyester, polyethylene, polypropylene, cellulose acetate and similar films. The adhesive coating 110 and 120 are temporarily protected by the anti-stick protective sheets 122 and 124 respectively. The protective sheets 122 and 124 are comprised of paper or similar web material having anti-stick coatings, such as cured dimethyl silicone or wax. These anti-stick protective sheets 122 and 124 have significantly lower surface energy than the surface tension of the adhesive coatings 110 and 120, and will therefore separate easily from the adhesive coatings. Typically the surface energy of the anti-stick protective sheets 122 and 124 is less than about 80%, preferably less than about 50%, more preferably ranges up to 25% of the surface tension of the adhesive coatings. Spacer 106 is comprised of a disposable material such as paper, cardboard, or foam pad, and the spacer has both faces covered with adhesive coatings 112 and 118. The adhesive coatings 112 and 118 have surface tensions significantly greater than the surface energies of appliqués 114 and 116 respectively, and are thereby adapted to temporarily hold the appliqués. Typically the surface tension of the adhesive coatings 112 and 118 is greater than about 125%, preferably greater than about 200%, more preferably ranges above 400% of the surface energy of the appliqués 114 and 116.

In use of the apparatus 90, protective sheets 122 and 124 are stripped from marker installation assembly 91 and the exposed adhesive surface 120 is pressed against and along the periphery of the active surface 34a of the screen 34 disposed in open cassette 2, until firmly secured. Fully closing and reopening cassette 2 causes appliqué 116 to permanently affix to the active surface 14a of the screen 14, and the spacer 106 to separate at one of its adhesive surfaces 112 or 118, permitting removal and disposal of the spacer 106. Appliqués 114 and 116 are permanently transferred to their respective intensifying screens 34 and 14, and markers 58 and 60 are then lined up exactly one over the other. The above described apparatus represents the preferred manner of installing markers on intensifying screens. Optionally, a single light-opaque marker having an adhesive surface is manually attached to either intensifying screen.

The invention has been described in detail with particular reference to the preferred embodiments thereof, but it will be understood that additional variations and modifications may suggest themselves to one skilled in the art, all falling within the scope of the invention as defined by the subjoined claims.

What is claimed is:

1. A radiographic film cassette for exposing a sheet of film to X rays projected along an X ray path by an X ray tube, comprising:
   (a) a cover having an inner surface defining a recess for receiving said film sheet;
   (b) a base having an inner surface adapted to close upon said cover for securing said film sheet;
   (c) a first intensifying screen immovably disposed within said recess between said film sheet and the inner surface of said cover;
   (d) a first marker permanently fixed to said first intensifying screen and adjacent to said film for intersecting a first portion of said X ray path during exposure, said marker being light-opaque and chirally asymmetric;
   (e) a second intensifying screen immovably disposed between said film sheet and the inner surface of said base;
   (f) a second marker permanently fixed to said second intensifying screen adjacent to said film for intersecting a second portion of said X ray path during exposure, said marker being light-opaque;
   said film sheet, upon exposure, bearing a composite image of each of said markers.

2. A film cassette as recited in claim 1, wherein said second marker has dimensions greater than said first marker and is so situated within said X ray path that said first portion is overlapped by said second portion.

3. A film cassette as recited in claim 1, wherein one or both of said first and second markers are cutouts in the first and second intensifying screens respectively.

4. A radiographic film cassette for exposing a sheet of film to X rays projected along an X ray path by an X ray tube, comprising:
   (a) a cover having an inner surface defining a recess for receiving said film sheet;
   (b) a base having an inner surface adapted to close upon said cover for securing said film sheet;
   (c) a first intensifying screen immovably disposed within said recess between said film sheet and the inner surface of said cover;
   (d) a first marker permanently fixed to said first intensifying screen adjacent to said film for intersecting a first portion of said X ray path during exposure, said marker being light-opaque;
   (e) a second intensifying screen immovably disposed between said film sheet and the inner surface of said base;
   (f) a second marker permanently fixed to said second intensifying screen adjacent to said film for intersecting a second portion of said X ray path during exposure, said marker being light-opaque and chirally asymmetric;
   said film sheet, upon exposure, bearing a composite image of each of said markers.

5. A film cassette as recited in claim 4, wherein said first marker has dimensions greater than said second marker and is so situated within said X ray path that said second portion is overlapped by said first portion.

6. A film cassette as recited in claim 4, wherein one or both of said first and second markers are cutouts in the first and second intensifying screens respectively.

7. An apparatus for installing a plurality of light-opaque markers on active sides of a plurality of intensifying screens disposed in an X ray film cassette, comprising;
   (a) a first marker, being light-opaque and chirally asymmetric;
   (b) a second marker, being light-opaque and having dimensions greater than said first marker;
   (c) first and second appliqué sheets carrying said first and second markers, respectively, each of said sheets having an adhesive surface in contact with an anti-stick protective sheet, adapted for removal to unmask adhesive thereon; and
   (d) spacing means comprising a spacer sheet having first and second planar surfaces provided with adhesive coating adapted for temporary contact with said first and second appliqué sheets, respectively, to thereby form a marker installation assembly;
   whereby disposition of said marker installation assembly on an active side of one of said intensifying screens with said adhesive surfaces unmasked is operative, upon closing said cassette, to adhesively secure said appliqué sheets to said intensifying screens in an aligned condition.

8. Apparatus as recited in claim 7, wherein each of said appliqué sheets is composed of a transparent material.

9. Apparatus as recited in claim 7, wherein said anti-stick protective sheet comprises a transparent material.

10. Apparatus as recited in claim 7, wherein said anti-stick protective sheet is selected from the group consisting of silicone coated paper and wax paper.

11. Apparatus as recited in claim 7, wherein said anti-stick protective sheet has a surface energy that is less than the surface tension of said adhesive surface.

12. Apparatus as recited in claim 7, wherein said adhesive surface of each of said first and second appliqué sheets comprise a pressure sensitive adhesive.

13. Apparatus as recited in claim 7, wherein said adhesive coating has a surface tension greater than the surface energy of said appliqué sheets.

14. Apparatus as recited in claim 7, wherein each of said appliqué sheets is a member selected from the group consisting of cellophane, polyvinyl chloride, polyester, polyethylene, polypropylene and cellulose acetate.

15. Apparatus as recited in claim 7, wherein said anti-stick protective sheet has a surface energy that is less than about 80% of the surface tension of said adhesive surface.

16. Apparatus as recited in claim 15, wherein said pressure sensitive adhesive is a member selected from the group consisting of polyvinyl ethyl ether, polyisobutylene and acrylate copolymer.

17. Apparatus as recited in claim 16, wherein said surface tension of said adhesive coating is greater than about 125% of said surface energy of said appliqué sheets.

* * * * *